United States Patent [19]

Howell

[11] Patent Number: 5,247,835
[45] Date of Patent: Sep. 28, 1993

[54] PILE TESTER

[76] Inventor: Mark I. Howell, 23 Windsor Court, Clifton, Bristol BS8 4LJ, England

[21] Appl. No.: 773,930
[22] PCT Filed: May 4, 1990
[86] PCT No.: PCT/GB90/00702
§ 371 Date: Nov. 4, 1991
§ 102(e) Date: Nov. 4, 1991
[87] PCT Pub. No.: WO90/13805
PCT Pub. Date: Nov. 15, 1990

[30] Foreign Application Priority Data

May 6, 1989 [GB] United Kingdom ................ 8910443

[51] Int. Cl.$^5$ ............................................. G01N 3/34
[52] U.S. Cl. .................................. 73/12.01; 173/112; 173/202
[58] Field of Search ............... 73/12; 173/112, 120, 173/121, 202

[56] References Cited

U.S. PATENT DOCUMENTS

| | | | |
|---|---|---|---|
| 1,572,046 | 2/1926 | Seiler | 173/120 |
| 2,455,270 | 11/1948 | Ravella | 173/120 |
| 3,268,013 | 8/1966 | Sussman | 173/121 |
| 3,888,108 | 6/1975 | Brands | 73/12 |
| 4,359,890 | 11/1982 | Coelus | 73/12 |
| 4,682,490 | 7/1987 | Adelman et al. | 73/12 |
| 4,967,587 | 11/1990 | Sirica | 73/12 |

FOREIGN PATENT DOCUMENTS 153621 11/1920 United Kingdom .................. 73/12

OTHER PUBLICATIONS

Soviet Journal of Nondestructive Testing, vol. 23, No. 2, Feb. 1987, Plenum Publishing Corp., New York, US.
Patent Abstracts of Japan, vol. 13, No. 104.
Journal of Physics E: Scientific Instruments, vol. 17, 1984.

*Primary Examiner*—Michael T. Razavi
*Assistant Examiner*—Timothy J. May
*Attorney, Agent, or Firm*—Larson and Taylor

[57] ABSTRACT

A self-contained unit has a probe (N) urgeable against a structure to be tested, a shock assembly (H, I, J, F, M) for applying a shock to the structure through the probe (N), and a transducer (A, B, C) for receiving resulting vibrations from the structure through the probe (N) and providing electrical output data. The unit also includes a memory (b) for storing the data. The unit has a tubular body (E) in which the transducer (A, B, C) is receivable. The transducer (A, B, C) is linked to a weight (H) and springs (G, I) such that urging the probe (N) against a structure progressively compresses springs (G, I), drives the enclosure (A, B, C) into the body (E) and raises the weight (H) until the weight is suddenly released and hits the transducer (C) to supply the shock.

3 Claims, 2 Drawing Sheets

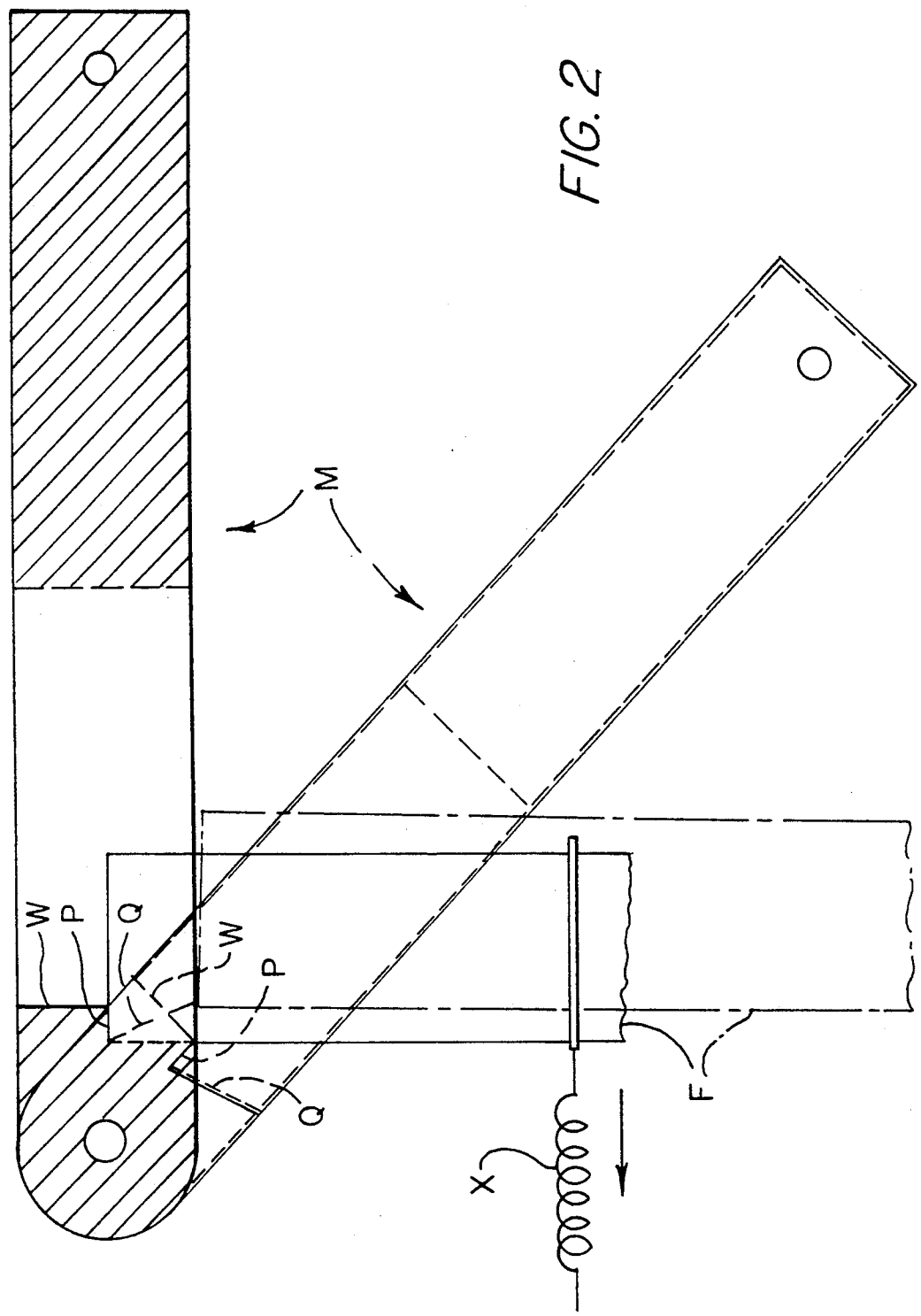

ns unsuitable for publication# PILE TESTER

TECHNICAL FIELD

This invention relates to apparatus and methods for the evaluation of the integrity of building structures and the like, particularly foundation piles for buildings and structures.

BACKGROUND ART

It is known to apply a mechanical shock to a pile, detect the resulting vibrations of the pile, and analyse them to provide data about the pile. Such methods are known variously as 'acoustic', 'sonic', or 'transient dynamic' pile survey. Essentially, the method measures the pile-head's vertical motions in response to a mechanical shock. The shock may be generated by a manually-delivered blow downwards on the pile-head, sometimes via a 'load cell' which measures the force of the initial shock, and the subsequent vertical motions of the pile-head, or it may be that the concrete is struck directly and the resulting motions are registered by a velocity or acceleration transducer firmly attached to the concrete nearby the shock position.

The shock causes the concrete to be momentarily compressed, and vertical motions of waveform approximating a decaying sinusoid follow the blow, as measured at the pile-head. In descending the column of the pile, reflection of proportions of the shock wave occur wherever the column varies in cross-sectional area, or in density. On returning to the pile-head such reflections 'interfere' with the decaying sinusoid motions there, and interpretation of this resultant complex waveform enables predictions as to the existence of defects in the pile column, and confirmation or otherwise that it is of the correct length. The technique is now well-established in the Construction Industry.

There are three essential conditions for the acquisition of the pile shock vibration data:

1. the vibration transducer must be held in firm contact with the concrete of the pile-head
2. a shock (or 'impulse') must occur
3. a record of the vertical vibration motions of the transducer (and thus the pile-head) must be made In addition, a means should exist for recording the identity (its site number) of the pile under test.

In many site circumstances, access to the piles may not be straightforward. They may be relatively distant from a position to which a vehicle can be conveniently brought, or the pile-heads may be covered in mud, water or other site debris, and site plant and other obstacles may be inimical to the presence of the recording apparatus and the normal preparations necessary for the tests to proceed.

Existing methods are slow in execution, and may be difficult or impossible to carry out in the face of such usual construction site obstacles as mud, flooding, deep trenching, shuttering, site traffic and so on.

DISCLOSURE OF THE INVENTION

It is an objection of this invention to provide an apparatus that can acquire the necessary information to enable an evaluation of piles' soundness and fitness for their purpose in as short a time as possible and with the minimum possible disruption of the normal site activities, and with minimum hazard to the pile surveyor and other site personnel.

According to the present invention there is provided apparatus for use in testing structures, comprising a self-contained unit comprising shock means for delivering a mechanical shock of predetermined magnitude to a structure; transducer means for sensing vibrations of a structure caused by said shock and producing a corresponding electrical signal; and memory means coupled to said transducer means for storing electrical signals from it;

said shock means comprising potential energy storage means adapted to be gradually charged and suddenly discharged to deliver said mechanical shock; wherein the apparatus includes a probe arranged to transmit said shock from said shock means to a structure, and to transmit said vibrations to said transducer means; and the probe is arranged to effect said gradual charging by a force acting on the probe when the probe is urged against the structure to be tested.

Suitably the shock means includes a mass and means whereby it is guided to strike, with constant force, a rigid assembly containing the transducer, causing the transducer to produce a voltage output representing its mechanical displacements along the axis of the assembly.

In the development of preferred embodiments of the invention, account has been taken of all the obstacles to the testing procedures normally encountered on construction sites, and an apparatus has been developed which can be deployed rapidly and reliably, and with minimal or no interference with the usual site activities and traffic.

BRIEF DESCRIPTION OF THE DRAWINGS

FIG. 2 is a view on a larger scale of portions of the drop-weight mechanism of the FIG. 1 embodiment.

BEST MODE FOR CARRYING OUT THE INVENTION

Figure 1:
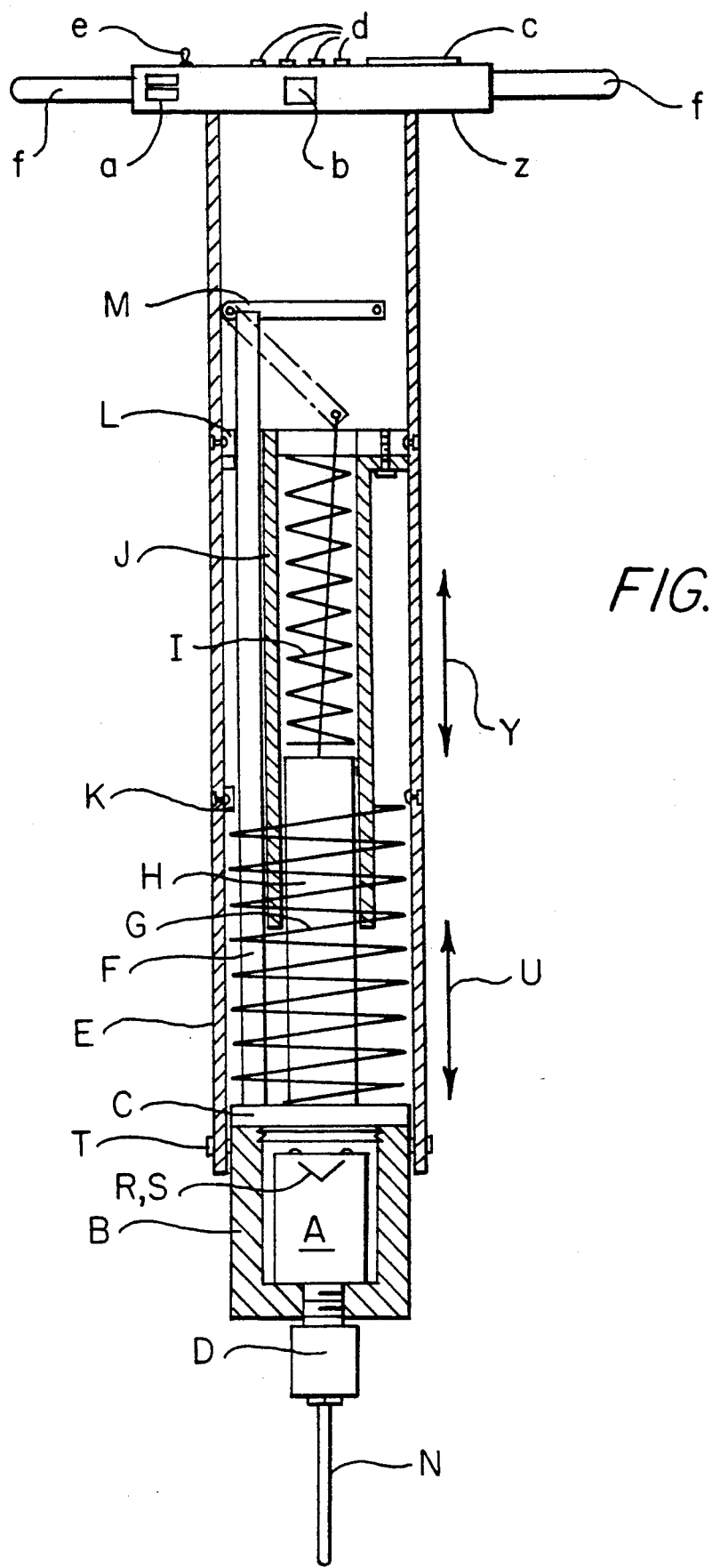
FIG. 1 is a schematic axial section through an apparatus embodying the invention.

The illustrated apparatus has a cylindrical outer sleeve E. Adjacent its lower end there are a plurality of longitudinally extending guide slots. A transducer carrying chamber B has the form of a cylindrical cup, whose interior cavity opens into the interior of the sleeve E. Within the cup cavity there is an electromagnetic velocity, acceleration or displacement transducer assembly A having transducer terminals R, S. A shaft passes threadedly through an aperture in the base of the cup and bears a chuck D in which a replaceable steel probe or contact rod N selected to be of suitable dimensions for the job in hand is gripped. The mouth of the cup is threaded to receive a lid C. Transverse guide pins T (one of which can be seen in FIG. 1) extend outwardly from the cup, through respective guide slots. The chamber B is telescopically receivable within the sleeve, its maximum travel being indicated by an arrow U.

A push-rod F extends within the sleeve E. Its lower end rests on the lid C of the chamber B. Its upper end and associated parts of a drop-weight mechanism are shown in FIG. 2. A drop-weight lifting lever M is pivotally mounted inside the sleeve E adjacent the top of the pushrod F so as to be pivotable upwardly from the configuration shown in broken lines in FIG. 1 in which it extends downwardly at an angle to the sleeve's axis.

The lever M has a slot bounded adjacent the pivot by a stepped surface formed of a rod displacement profile Q, a ratchet profile P and a transverse portion W. The rod displacement profile Q extends from the longitudinal axis of the lever M to the lower edge thereof, angled slightly towards the distal end of the lever M. The ratchet profile P extends from the axial end of the displacement profile Q along the longitudinal axis, away from the pivot. The transverse portion W extends from the ratchet profile P transversely to the longitudinal axis.

A spring X (FIG. 2) attached to a collar (FIG. 2) on the rod F urges the rod leftwards (with reference to the orientation shown in FIGS. 1 and 2) so that its top end tends to contact the stepped surface P, Q, W.

The distal end of the lever M has a line anchored to it. This carries a drop-weight H which is displaceable within a drop-weight guide cylinder J. At upper and intermediate regions of the sleeve E, there are internal drop-weight guide spacing rings K, L which hold the guide cylinder J centrally within the sleeve E. A transducer carrying-chamber compression spring G is engaged between the intermediate ring K and the chamber lid C. A drop-weight acceleration spring I is engaged between the top of the drop-weight H and the upper spacing ring L.

In use, pressure is applied downwards on the enclosing sleeve E, compressing transducer chamber compression spring G, which forces transducer chamber B, C against the concrete of the pile-head by way of the contact rod N held in the chuck D. The pressure might alternatively be maintained by pneumatic, magnetic or other known means of exerting pressure, acting on the transducer chamber.

As the transducer chamber rises in the tube, push-rod F engages the ratchet contour of the drop-weight lifting lever M, raising the drop-weight lifting lever M, which raises the drop-weight H against the drop-weight accelerating spring I. As the lever approaches the horizontal, the push-rod is forced away from the ratchet P by the profile Q (FIG. 2). The drop-weight is released and is accelerated by spring I and gravity towards the transducer cover C, striking it. The weight's travel is indicated by arrow Y. The force is transmitted to the concrete via the chamber sides and base B, chuck D and contact-rod N; the whole assembly being held during this time in firm contact with the concrete by spring G. Alternative simple hoist and release mechanisms could feature toothed wheels and/or rods, and the acceleration spring might be replaced by pneumatic or magnetic means of exerting pressure, or it might be omitted altogether, leaving acceleration of the mass to be caused by gravity alone.

The transducer assembly A will produce at its terminals R, S an alternating voltage proportional to the vibration motions of the pile-head along the axis of the chamber and the tube in response to the shock. Thus a single downward motion of the complete assembly will result in a voltage waveform representing the pile-head vibration response to a shock at the tip of rod N.

At the top of tube E an enclosure Z may be mounted containing solid-state memory circuitry, numerical keyboard, voltage-level attenuator and liquid crystal display, capable of storing by known digital means vibration motion representations of up to 120 shocks, and transferring these at a later time to a computer for analysis, processing and paper print-out. For example, such a print-out may comprise an oscillation trace, a listing of data calculated by the computer (e.g. Toe reflection time, decay rate of oscillation, and estimated length of pile), and a listing of identification data at least some of which are input on site, using the keyboard of the apparatus. Such data may include some or all of the pile number, the impulse number, identification of the client and site, and the date and time.

The enclosure Z on the apparatus may house batteries a, a memory b employing removable memory cards, a display screen c, a keyboard d, and a multiposition switch e. Handles f for operating the device may extend on either side.

The switch e may be a four-position key-operated switch, for selecting the modes: "off", "review stored data", "record" and "erase memory card". The keyboard is used to enter the pile numbers, adjust the sensitivity (rarely needed), and review the stored data and waveforms. The overall weight of the unit is desirably below 14 lbs 7(kg).

With its low weight and rapid sounding capacity the apparatus can complete surveys of fifty or a hundred piles in one or two hours. Even where there are obstructions on the site and the piles have not been prepared for testing, site hold-ups are negligible. Because the apparatus makes contact with the pile-head through its single steel probe, it can easily operate through reinforcing bars and cages and overlying water, mud and loose rubble. The lightness of the unit also means that it can easily be carried hundreds of meters to piles where vehicles cannot reach.

I claim:

1. Apparatus for testing foundation piles comprising a self-contained unit which comprises:

an elongate body;

laterally projecting handle means at an upper region of the body;

a transducer means for sensing vibration and producing corresponding electrical signals;

memory means coupled to said transducer means for storing electrical signals from said transducer means;

a carrier for said transducer means, said carrier being mounted to said body so that said body is longitudinally displaceable relative to said carrier;

an elongate probe coupled to said carrier and projecting downwardly from the carrier, said probe projecting downwardly from said body to an extent that is variable by displacing said body relative to said carrier; and shock means mounted to said body for delivering a pre-determined mechanical shock to said probe; said shock means comprising potential energy storage means including lever means coupled to said body and said carrier so that said relative displacement of the body causes the lever means to pivot; and a weight coupled to the lever means so as to be lifted thereby, and the arrangement being such that downward displacement of the body relative to the carrier causes upward displacement of the weight relative to the carrier and to the body; said shock means further including release means for suddenly releasing the weight after the weight has been raised a predetermined distance so as to impart a mechanical shock to said probe; the arrangement being such that the apparatus can be held by the handle means and the probe can then be urged downwardly against a foundation pile, with continuing downward pressure producing downward displacement of the body relative to the carrier and a consequent raising of the weight, and a subsequent release of the weight by the releasing means so as to administer a shock which is transmitted by means of the probe to the foundation pile; the shock and subsequent vibrations being sensed by the transducer means which transmits corresponding signals to the memory means for storing by said memory means.

2. Apparatus according to claim 1 wherein said potential energy storage means further includes spring means coupled to the weight so as to urge the weight downwardly so that the spring means is energized as the weight is lifted.

3. Apparatus according to claim 1 wherein said lever means comprises a lever pivoted at a pivot to said body and coupled to said weight at a region remote from the pivot; and a transmission rod extending between said carrier and a region of said lever close to said pivot such that upward movement of said rod tends to cause upward pivoting of said lever; and wherein said release means comprises a shaped portion of the lever which is arranged to push the rod out of engagement with the lever which the lever has pivoted upwardly to a predetermined extent.

* * * * *